(12) United States Patent
Barone

(10) Patent No.: US 8,591,573 B2
(45) Date of Patent: Nov. 26, 2013

(54) PROSTHETIC VALVE FOR INTRALUMINAL IMPLANTATION

(76) Inventor: Hector Daniel Barone, Buenos Aires (AR)

( * ) Notice: Subject to any disclaimer, the term of this patent is extended or adjusted under 35 U.S.C. 154(b) by 784 days.

(21) Appl. No.: 12/330,039

(22) Filed: Dec. 8, 2008

(65) Prior Publication Data

US 2010/0145438 A1 Jun. 10, 2010

(51) Int. Cl.
*A61F 2/06* (2013.01)
*A61F 2/24* (2006.01)

(52) U.S. Cl.
USPC .......... 623/2.1; 623/1.24; 623/2.17; 623/2.19

(58) Field of Classification Search
USPC ................ 623/2.17, 2.19, 1.24, 2.1
See application file for complete search history.

(56) References Cited

U.S. PATENT DOCUMENTS

| | | | |
|---|---|---|---|
| 7,018,406 B2 * | 3/2006 | Seguin et al. | 623/2.1 |
| 7,025,780 B2 * | 4/2006 | Gabbay | 623/2.13 |
| 7,311,730 B2 * | 12/2007 | Gabbay | 623/2.38 |
| 7,534,261 B2 * | 5/2009 | Friedman | 623/2.17 |
| 2005/0137689 A1 * | 6/2005 | Salahieh et al. | 623/2.11 |
| 2007/0142907 A1 * | 6/2007 | Moaddeb et al. | 623/2.11 |
| 2007/0162103 A1 * | 7/2007 | Case et al. | 623/1.13 |
| 2008/0161909 A1 * | 7/2008 | Kheradvar et al. | 623/2.11 |
| 2008/0161911 A1 * | 7/2008 | Revuelta et al. | 623/2.17 |
| 2008/0208329 A1 * | 8/2008 | Bishop et al. | 623/2.11 |
| 2008/0215144 A1 * | 9/2008 | Ryan et al. | 623/2.18 |
| 2009/0082857 A1 * | 3/2009 | Lashinski et al. | 623/2.18 |
| 2010/0204785 A1 * | 8/2010 | Alkhatib | 623/2.37 |

FOREIGN PATENT DOCUMENTS

EP 1 872 743 A1 1/2008
WO 2006/127756 A2 11/2006

OTHER PUBLICATIONS

European Search Report Dated March 16, 2010.

* cited by examiner

*Primary Examiner* — Bruce E Snow
*Assistant Examiner* — Brian Dukert
(74) *Attorney, Agent, or Firm* — Norris McLaughlin & Marcus, P.A.

(57) ABSTRACT

A prosthetic valve assembly configured to be intraluminally implanted into a lumen of a patient to replace a native deficient valve, the valve assembly comprising an outer support for expanding and anchoring against a lumen wall of the patient, a core valve support made of a collapsible and self-expanding material to expand and anchor into the outer support once anchored against the lumen wall, and a plurality of flexible leaflets fixed to the core valve support in a manner that the leaflets are independent from the outer support.

21 Claims, 7 Drawing Sheets

PROSTHETIC VALVE FOR INTRALUMINAL IMPLANTATION

BACKGROUND OF THE INVENTION

1. Field of the Invention

The present invention relates to the field of prosthetic medical devices for implantation into a patient and more particularly refers to a valve assembly configured to be intraluminaly delivered into a lumen of a vessel of a patient and assembled at a location into the lumen where a native valve of the patient is deficient.

2. Description of the Prior Art

It has been a practice to open the thorax of a patient when a defective corporeal valve had to be repaired. Particularly in cardiac valves, the traditional surgery has been a very risky procedure involving the steps of opening the thorax, providing extracorporeal blood circulation, and surgically opening the heart to remove the defective valve and implanting a new one, namely a prosthetic valve generally sutured into the blood vessel having the deficient natural or native valve.

In the last years, a less risky and less invasive technique has consisted of delivering a prosthetic valve into the blood vessels of the patient and implanting the new valve at the desired location, and implanting the new prosthetic valve directly onto the native defective one. Some prosthetic valves for transluminal delivery are disclosed in several documents. U.S. Pat. No. 5,370,685 discloses a prosthetic valve comprising a flexible cylindrical sleeve with three cusps that are shown free to move in a direction to permit the blood flow and capable of moving in an opposite direction to prevent backflow. The sleeve is fixed at a bottom edge thereof to a mounting ring made of a self-expanding structure to expand, upon release of any external pressure, to rest against a vascular wall. In order to be anchored in the wall, the mounting ring is provided with mounting pins to fix the valve at the designated valve situs.

The above described valve is of the type that are directly anchored in the vessel wall by means of any anchoring means such as hooks, pins and the like. This direct fixation while simple is still capable of being improved to prevent migration and misplacing of the valve. A cardiac valve must be fixed at the correct place and properly anchored in place to resist the constantly changed vessel diameter and turbulent blood flow.

To solve at least some of the problems of insecure fixation another type of prosthetic valve is comprised of a valve and a support structure or stent that is fixed against the vessel wall along a larger area of the vessel wall. U.S. Pat. No. 7,329,278 discloses a valve comprising a support stent or armature made of shape memory material, and configured to expand against the vessel wall and anchor therein. The armature is made of wire and has a general cylindrical shape with a central support band for placing against a vessel annulus and end portions for placing above and below the annulus, respectively. The valve also comprising the valve leaflets made of biological material (preserved human or animal valve leaflets) or of synthetic material, such as a polymer. The leaflets are fixed at their base to the central band of the armature or stent and the cusps of the leaflets are fixed to the armature through commissure points. In other words the upper part of the leaflets are fixed, by suture, for example, to the armature. In movement of opening and closing the vessel to permit/prevent the blood flow, the leaflets pull from the commissure, when closing, and impact against the armature, when opening, this causing the failure of the valve along the millions of cycles along the life time.

For a correct implantation of the valve, the same must be placed exactly at the vessel annulus and in a manner to guarantee no leaks. The annulus is, sometimes, calcified therefore it does not offer e proper set for the new valve. The valves of the type that the support ring thereof is directly anchored at the annulus must be placed adequately in order to accommodate to the annulus. If misplaced, migration is to be expected.

In the valves employing a self expandable stent support, such stent support needs to be very long to prevent migration. Thus the self expandable stent inconveniently protrudes into the ventricle and into the first segment of the aorta. Distinct from this, the valves with balloon expandable stent support are shorter because the anchorage is better and migrations seems to be less frequent. However, with a balloon expandable stent support a damage to the valve leaflets is to be expected because the leaflets are mounted into the stent and when the stent is expanded by the balloon, the leaflets, made of flexible synthetic or natural tissue and placed between the balloon and the stent, will be squeezed against the stent by the balloon exerting the necessary radial expanding force, during inflation.

In addition to the foregoing, the flexible valve material, natural tissue or synthetic, is directly fixed to the stent in a manner that upper points of the flexible leaflets are fixed to the stent. These anchoring points, made by suturing for example, are continuously subject to concentrated stress each time the leaflets move to a close position.

Under the above circumstances it would be very convenient to have a new valve assembly with the advantages of the valves having a stent, thus improving the anchoring of the valve assembly in the vessel wall but without the drawbacks of these conventional valves relating to the stress of the commissure points where the material of the valve leaflets fail under fatigue stress by cycling pulling effect as well as without the drawbacks of the known intraluminaly-delivered valves having the leaflets material compressed and probably damaged when remaining between the outer support stent and the balloon expanding the assembly to anchor it in the vessel.

SUMMARY OF THE INVENTION

It is therefore an object of the invention to provide a new valve assembly providing a reliable anchoring for the assembly into a lumen of a vessel of a patient and having valve means capable of moving between an open and a close position without substantial subjecting the valve means to stresses at any concentrated point thereof.

It is still another object of the present invention to provide a new valve assembly for intraluminal delivery into a lumen of a patient comprising an outer support to guarantee the adequate anchoring and placing and an inner valve means to be mounted into the outer support.

It is a further object of the present invention to provide a prosthetic valve assembly configured to be intraluminally implanted into a lumen of a vessel of a patient to replace a native deficient valve, the valve assembly comprising an outer support for expanding and anchoring against a lumen wall of the patient, a core valve support made of a collapsible and self-expanding material to expand and anchor into the outer support once anchored against the lumen wall, and a plurality of flexible leaflets fixed to the core valve support in a manner that the leaflets are independent from the outer support.

It is a further object of the present invention to provide a prosthetic valve assembly for intraluminal implantation into a lumen of a vessel of a patient for replacing a native deficient valve, the valve assembly comprising:

an outer balloon expandable support made of a collapsible material and configured to be expanded for anchoring against a lumen wall of the patient and forming a waist section, a core valve support comprising a collapsible and self-expanding support ring with a plurality of flexible posts upwardly extending from the ring, the core valve support being configured to be collapsed for intraluminal implantation and being configured to expand into the lumen and the outer balloon expandable support once the outer balloon expandable support is anchored against the lumen wall, and a plurality of flexible leaflets pivotally connected to the collapsible and self-expanding support ring and posts and configured to move between an open position for permitting a blood flow through the valve assembly and a close position for preventing a backflow through the valve assembly.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
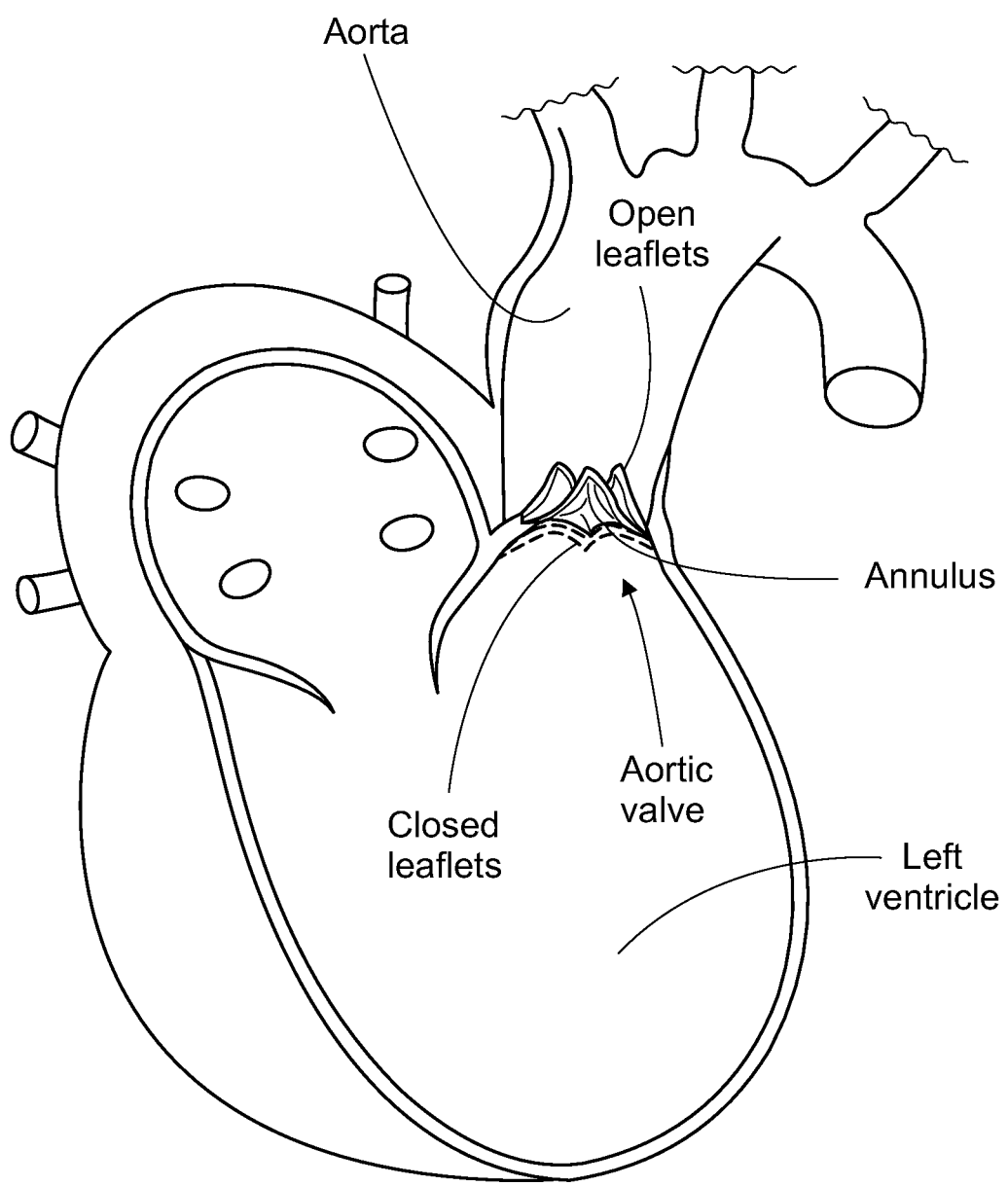
FIG. 1 shows a cross-section of a human heart with an aortic native valve shown in solid lines in the open position and in phantom lines in the closed position.

Now referring in detail to the drawings, FIG. 1 shows a cross sectional view of a human heart wherein an aortic valve is shown for permitting blood flow from the ventricle towards the aorta and to prevent backflow. The normal valve is a tricuspid valve with three leaflets or cusps that move upwardly to open the valve, as shown in solid lines, and downwardly to close the valve as shown in phantom lines. When this natural valve is deficient or defective it must be repaired or replaced by a prosthetic valve.

Figure 2:
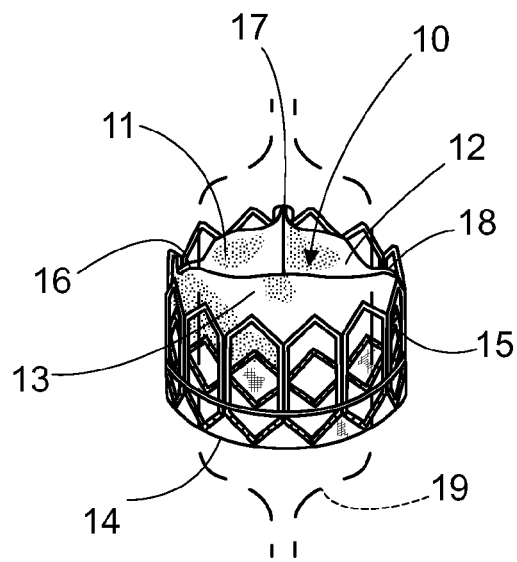
FIG. 2 shows a perspective view of a prosthetic valve of the prior art comprising a valve and a balloon expandable support stent.

FIG. 2 shows a prosthetic valve of the prior art comprising a central valve 10 comprising three leaflets or cusps 11, 12, 13, all made of any suitable natural or synthetic flexible material. By any proper means a base 14 of the central valve is affixed to a valve support 15 made of any suitable balloon-expandable material configured to be capable of being expanded and anchored by radial expansion against a lumen, such as the aortic root, of the patient, more precisely the annulus where the native valve is placed. The central valve has their cusps 11, 12, 13, most preferably an upper region of each cusp, affixed to valve support 15 by suture, for example, at commissure points 16, 17, 18. The leaflets or cusps move along a number of between 65-80 cycles per minute for the life of the patient. This is a pulsating stress concentrated in each point 16, 17, 18 with the result of the cusps failing by rupturing under fatigue tensions with the serious consequences for the patient.

Figure 3:
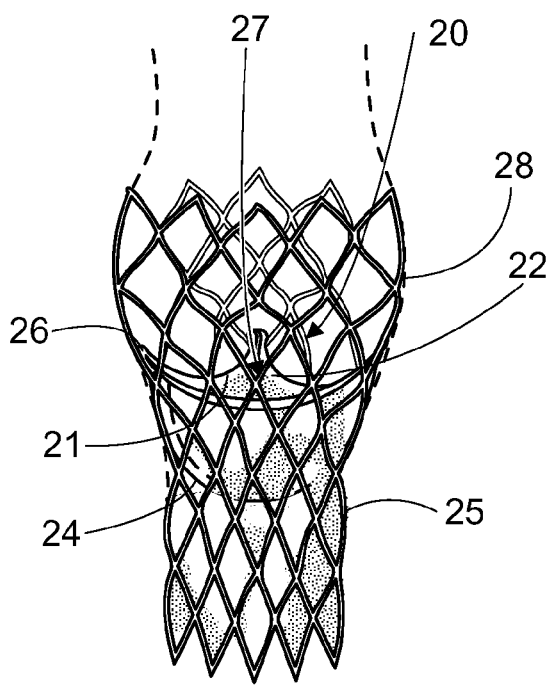
FIG. 3 shows a perspective view of another prosthetic valve of the prior art also of the type comprising a valve and a self expandable support stent.

FIG. 3 shows another prosthetic valve of the prior art also comprising a central valve 20 with three leaflets or cusps 21, 22, and another one not shown, all made of any suitable natural or synthetic flexible material. Base 24 of the central valve is affixed to a valve support 25 made of a self-expanding mesh capable of expanding and anchoring against a vessel or lumen of the patient, such as the annulus of the native valve. The central valve has their cusps, most preferably an upper region of each cusp, affixed to valve support 25 by suture, for example, at commissure points 26, 27, 28. Again, the movement of the cusps generate a pulsating stress concentrated in each point 26, 27, 28 causing the cusps failing by rupturing under fatigue.

In addition to the foregoing, a valve assembly of the type shown in FIG. 2, is implanted by a balloon that results in the potential damage of the natural or synthetic material valve. As it is shown in FIG. 2, if support stent 15 is made of a balloon expandable material a balloon 19, shown in phantom lines, must be placed passing into the central valve and leaflets. To anchor the support stent against the vessel lumen the balloon must be inflated to a radial expanded form as shown in FIG. 2. Under these conditions the leaflets and the entire central valve material is squeezed against the support stent and probably damaged. This effect can be found both in the valve system of FIG. 2.

Because of the above, outer support stent 25 must be preferably made of a self-expanding material. While this overcomes the above disclosed drawbacks of using a balloon, the valve system is not provided with the benefits and advantages of the balloon expandable stent supports that decreases the leaking effects. In effect, the self-expanding stents or supports continuously exerts a radial expanding force against the vessel walls during the life of the patient thus forcing and quite probably deforming by expansion the vessel walls with unpredictable consequences. Self expanding stents also fail to effectively prevent leaking occurrence, therefore generally the length of the stent is so large that an important portion thereof protrudes into the ventricle.

Distinct form the self expanding stents, a balloon expandable device is anchored against the vessel wall and the balloon may be inflated as desired to accommodate the shape of the stent, by selective radial deformation, to the dimensions of the vessel without exerting a progressive force once implanted and anchored. This accommodation of the shape of the support to the shape of the vessel guarantees a most proper and adequate anchoring also preventing any leaking future.

According to the invention, a new prosthetic valve assembly for intraluminal implantation into a lumen of a patient for replacing a native deficient valve. Most preferably, the invention provides for a valve assembly with their components shown in FIGS. 4-6 while FIG. 7 shows the valve assembly once assembled and anchored into the annulus region between the ventricle and the aorta where the native aortic valve is placed.

Figure 6:
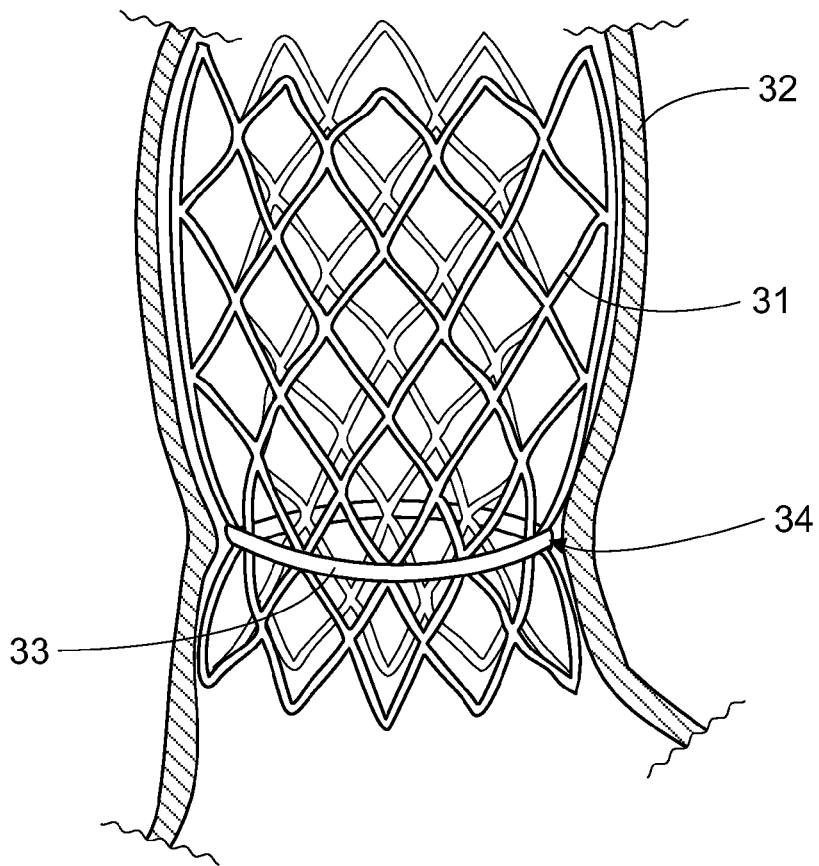
FIG. 6 shows a side elevational view of an outer balloon expandable support of a prosthetic valve according to the present invention, with the outer balloon expandable support implanted against the annulus wall at the site of the native aortic valve.
Figure 7:
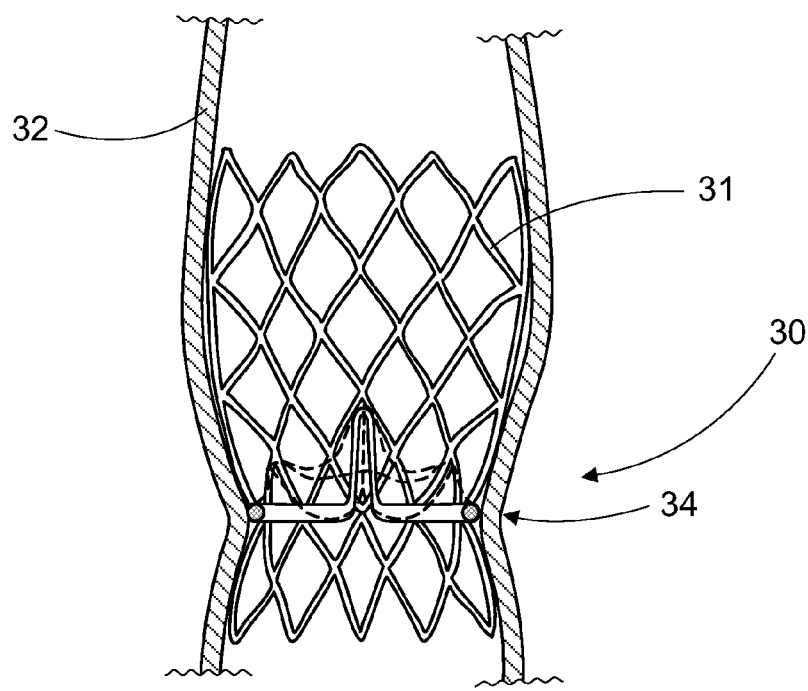
FIG. 7 shows a partial cross-section, side elevational, view of the outer balloon expandable support of FIG. 6, implanted in the native valve annulus, with the core valve support and leaflets anchored in the outer balloon expandable support.

The valve assembly of the present invention, generally indicated by reference number 30 in FIG. 7, comprises an outer balloon expandable support 31 made of a collapsible material and configured to be expanded for anchoring against a lumen wall 32 of the patient. Support 31 is an structure similar to a mesh or a stent made of metal, and most preferably of a medical steel capable of being expanded by a balloon against the vessel wall, more particularly at the annulus where the native aortic valve is located. Support 31 may be delivered into the vessel by a catheter technique using a delivery system wherein the support stent 31 is collapsed and placed around a flat balloon. Introduced by the delivering system into the vessel and placed in the desired location. When the catheter is at a location where the collapsed support must be anchored, the balloon/support is delivered out from the introducer and the balloon inflated, according to known techniques, to radially expand the support structure until the same is deployed as shown in FIGS. 6 and 7, and anchored against wall 32. Once the stent or support 31 is at least retained in the vessel wall, the balloon may be deflated in order to move it relative the support and inflate the balloon again in any desired particular section of the expanded support to better accommodate the shape thereof to the dimensions of the aortic root.

Support 31 is preferably provided with inextensible, or controllably extensible, means 33 to define a waist section 34 configured to be located at an anatomical valve section of the lumen and, preferably, at the location of the native aortic valve, namely the annulus as shown in FIG. 1. Inextensible means 33 is preferably employed to define a desired predetermined diameter to enhance and guarantee a firm retention of support ring into the waist section of support stent 31 and may be comprised of any suitable material capable of maintaining the desired diameter when the support ring is deployed into the stent support. In any event, the inextensible means may be extensible but in a less extent as compared to the stent structure 31. Means 33 may comprise a ring, a thread, a wire, suture and the like.

Figure 4:
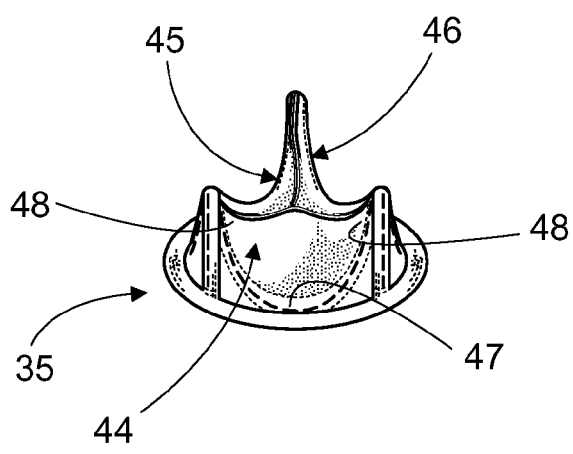
FIG. 4 shows a perspective view of a core valve support and leaflets of prosthetic valve according to the present invention.
Figure 5:
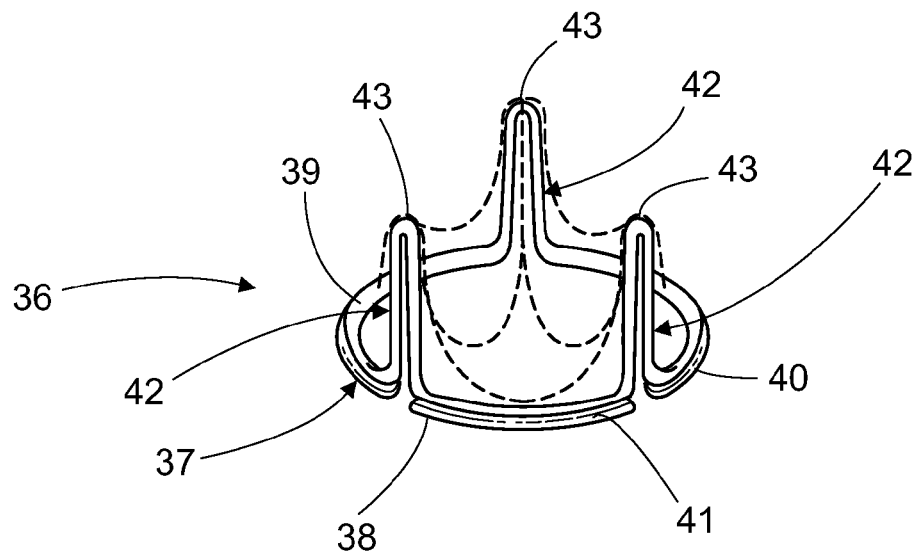
FIG. 5 shows a perspective view of the core valve support of FIG. 4 with the leaflets shown in phantom lines.

The inventive valve system also comprises a valve indicated by general reference 35 in FIG. 4 and comprised of the core valve support depicted in solid lines in FIG. 5 and indicated by general reference 36. Core support 36 in turn comprises a collapsible and self-expanding support ring 37 that may comprise only one closed ring or, as illustrated, a plurality of ring lengths 38, 39, 40 in a manner that ring 37 may be collapsed and introduced into a delivery system. More particularly, the entire core valve support and particularly the ring are configured to be collapsed for intraluminal implantation and being configured to expand into the lumen or duct of the patient and into outer balloon expandable support 31 once the outer balloon expandable support is already anchored against lumen or duct wall 32.

In order to be firmly retained or anchored into stent 31, ring 37 is provided with anchoring means capable of anchoring the support ring 37 to the waist section 34 of stent or outer balloon expandable support 31. Anchor means may comprise any hook, barbs and the like but preferably it comprises a "C" cross-section 41 formed in the collapsible and self-expanding support ring. The "C" cross-section, as better shown in FIG. 8, is open towards waist section 34 and configured to be coupled to the waist section once the support ring is radially expanded against stent 31.

Figure 8:
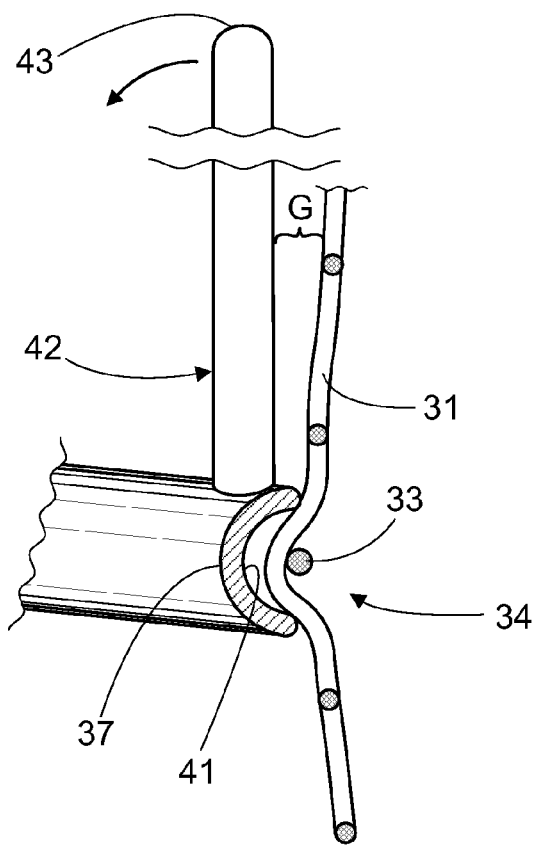
FIG. 8 shows a detailed partial cross-section, side elevation, view of the core valve support as mounted into the outer balloon expandable support.

Core support valve 36 also comprise a plurality of flexible posts 42 upwardly extending from ring 37 and having a corresponding flexible distal free ends 43 which are preferably capable of slightly pivoting relative to the base thereof connected to the ring, as shown by the arrows in FIG. 8.

Posts 42 may be connected to ring 37 as a separate parts or, according to the preferred embodiment, they may be an integral piece with the ring and ring lengths 38, 39, 40 and more particularly, posts 42 may be a continuation of of ring lengths 38, 39, 40 that extend upwardly and downwardly to conform each post. Therefore, posts 42 are made of the same material like ring 37.

Core valve support 36 and posts 42 may be made of any suitable self-expanding material such as medical steel, a shape memory material, like nitinol, Delrin®, polypropylene, and the like. Thus, valve 35 is delivered into stent 31 and deployed at the waist location 34 in order to anchor within the outer balloon expandable support and once the outer balloon expandable support is anchored against the lumen wall.

Valve 35 also comprises a plurality of flexible leaflets 44, 45, 46, preferably three leaflets, pivotally connected to the collapsible and self-expanding support ring 37 and posts 42 and configured to move between an open position for permitting a blood flow through the valve assembly and a close position for preventing a backflow through the valve assembly. The leaflets emulate the movement of the natural leaflets or cusps of the native valve. The leaflets 44, 45, 46 are shown in the close position in FIG. 4.

Each one of the plurality of leaflets has a valley portion 47 fixed to a corresponding portion 38, 39, 40, of support ring 37 and at least one crest portion 48 fixed at least to the flexible distal free end 43 of a corresponding post. Preferably, each leaflet includes two crests 48 with each crest 48 properly fixed to the free ends 43 of two adjacent posts 42. Leaflets 44, 45, 46 may be made of any flexible material such as natural tissue or synthetic material.

Figure 9:
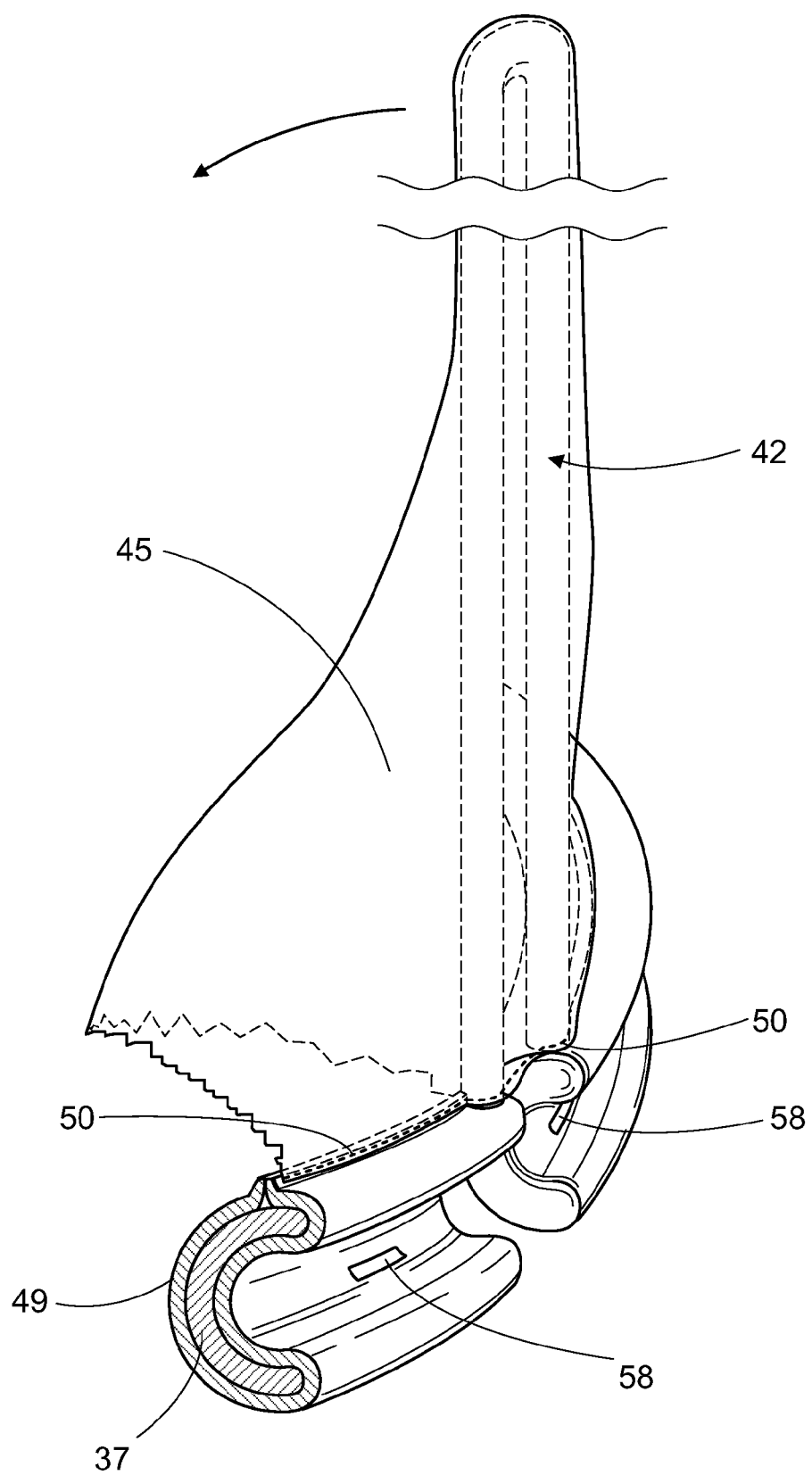
FIG. 9 shows a detailed partial cross-section, perspective view of the core valve support including a liner to enhance retention and/or sealing as well as to provide the means to fix the leaflets to the support ring.
Figure 10:
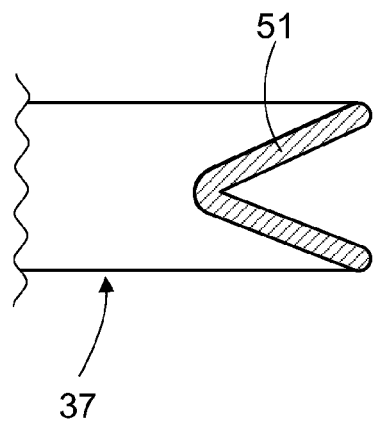
FIG. 10 shows a cross-section side elevation view of the support ring according to another embodiment of the present invention.

As shown in FIG. 9, support ring 37 and posts 42 are preferably covered by any of a textile material, a fabric, a polyester liner, indicated by reference 49, and each leaflet, indicated by 45 as an example, may be fixed by suture 50 to liner 49. Of course, the leaflets may be fixed to ring 37 by any other proper means, such as adhesives, clips, staples, etc.

Figure 11:
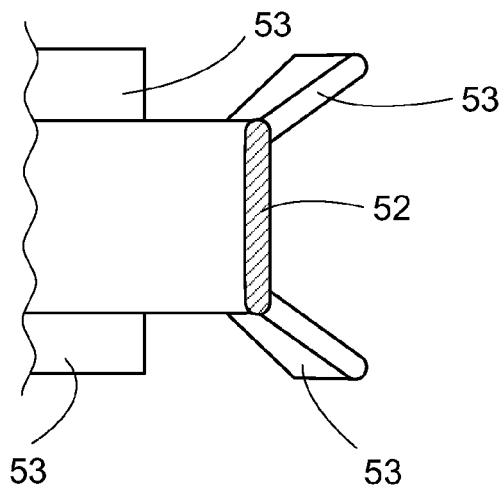
FIG. 11 shows a cross-section side elevation view of the support ring according to still another embodiment of the present invention.
Figure 12:
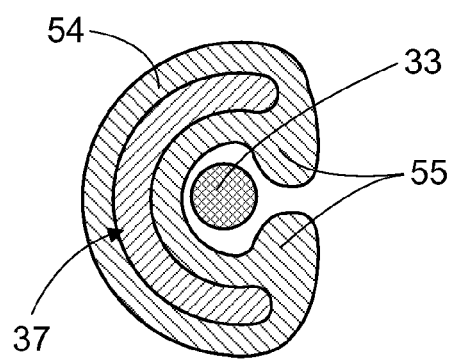
FIG. 12 shows a cross-section side elevation view of the support ring, as retained, by a C-shaped liner, in the inextensible means defining the waist section, according to a further embodiment of the present invention.

While the support ring has been shown as having a "C" cross section it is apparent to any person skilled in the art that the ring may have other shapes that permit to be radially anchored in the waist section of stent support 31. For example, ring 37 may have a "V" shaped cross section 51, or may be a simple ring 52 with opposite ears 53 uniformly arranged all around the ring, at upper and bottom edges of the ring, as shown in FIG. 11. Alternatively, the ring section, for example a "C" shape section as illustrated in FIG. 12, may be covered by a liner 54 defining thickened portions 55 with the same purpose of the above disclosed embodiments, namely to be kept retained around wire 33 or waist section of the stent support. The liner may also define a "C" shape without the need of the ring to have a "C" or "V" shaped section.

With the construction according to the invention, the crest of each leaflet, connected to free end 42, will pull inwardly from the end and the end, flexible and elastic, will yield upon the pulling of the leaflet without offering a rigid resistance thus extending the life time of the leaflet. Upon the opening of the leaflets to permit blood flow through the valve, the free ends may slightly move outwardly also accompanying the outward small movements of the leaflets but without being this outward movements so extended to permit the contact of the leaflet against stent 31 as it is the case of the valve systems of the prior art. In the known valve systems the leaflets when moving in the outward radial direction finally impact against the stent or support where they are fixed and, in addition to the cyclic pulling effect, with the radially inwardly movement, there is an impact effect against the stent during the radial outward movement. In the present invention, the moving parts of the leaflets are not in contact with the stent neither to pull therefrom nor to impact against the stent because there is a gap G as shown in FIG. 8.

Figure 13:
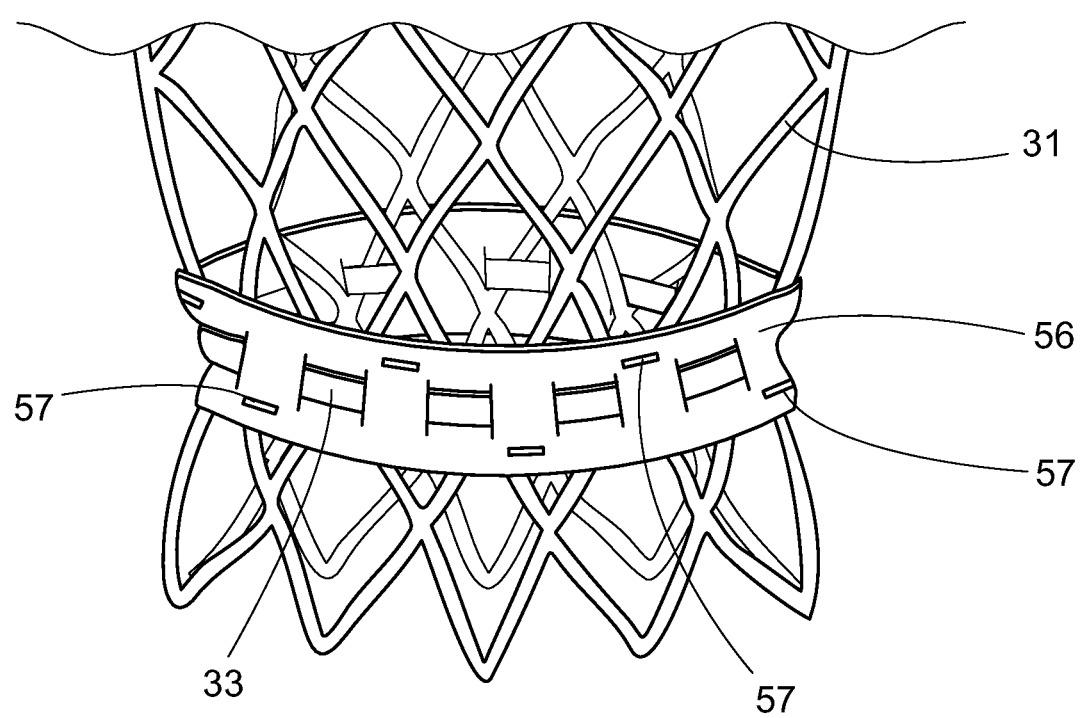
FIG. 13 shows a side elevation view of an outer balloon expandable support of a prosthetic valve according to the present invention, with a sealing material all around the waist section.

According to another embodiment of the invention, illustrated in FIG. 13, stent support 31 may be provided with sealing means 56 comprised of a material such as polyester, Teflon and the like in the shape of a fabric, textile, mat, film, and the like. Sealing material 56 may be fixed at the waist section of stent 31 by any proper retaining means such as adhesive, glue, suture, wire, etc. In the illustrated embodiment the sealing material is retained by inextensible means 33, such as a suture passing through the sealing material from one side to the other, as shown. Material 56 will seal against annulus wall, FIG. 1, in order to prevent any leak as well as it will retain any particles that me be released from the vessel or annulus wall during implantation of stent support 31.

In order to precisely place valve 35 in the correct position, at the waist section of support stent 31, inextensible means 33 and/or sealing material 56 may be provided with radio opaque marks duly arranged along the circumference of the waist section. Cooperatively, valve 35 will be provided with corresponding marks 58, FIG. 9, in order that, during installation, ring 37 is correctly deployed into stent 31. For example, marks 58 should be placed between upper and lower marks 57 shown in FIG. 13.

While preferred embodiments of the present invention have been illustrated and described, it will be obvious to those skilled in the art that various changes and modifications may be made therein without departing from the scope of the invention as defined in the appended claims.

I claim:

1. A prosthetic valve assembly for intraluminal implantation into a lumen of a patient for replacing a native deficient valve, the valve assembly comprising:
   an outer balloon expandable support having inextensible means and configured to be expanded radially beyond a smallest diameter defined by the inextensible means, for anchoring against a lumen wall of the patient and forming an inextensible waist section defined by said smallest diameter in the expandable support, wherein the support is balloon expandable, outwardly from the smallest diameter, above and below the waist section,
   a core valve support comprising a collapsible and self-expanding support ring configured to be anchored in the outer balloon expandable support once expanded, the support ring including a plurality of flexible posts upwardly extending from the ring and capable of moving radially inwardly, the core valve support being configured to be collapsed for intraluminal implantation and being configured to expand into the lumen and the outer balloon expandable support once the outer balloon expandable support is anchored against the lumen wall, the support ring including anchoring means for anchoring the support ring upwardly and downwardly to the inextensible waist section when the core valve support is anchored within the outer balloon expandable support and once the outer balloon expandable support is anchored against the lumen wall, wherein the support ring is anchored in the waist section such that the waist section and the inextensible means enter into the anchoring means, and
   a plurality of flexible leaflets pivotally connected to the collapsible and self-expanding support ring and posts and configured to move between an open position for permitting a blood flow through the valve assembly and a closed position for preventing a backflow through the valve assembly, wherein a gap is defined between the flexible posts and the balloon expandable support to prevent the posts and leaflets from entering into contact with the support during the movements between the open and closed positions.

2. The valve assembly of claim 1, wherein said outer balloon expandable support comprises a radially expandable stent.

3. The valve assembly of claim 1, wherein said inextensible waist section is configured to be located at an anatomical valve section of the lumen.

4. The valve assembly of claim 3, wherein said inextensible waist section comprises an inextensible ring.

5. The valve assembly of claim 4, wherein said inextensible ring comprises an inextensible thread.

6. The valve assembly of claim 4, wherein said inextensible ring comprises an inextensible wire.

7. The valve assembly of claim 1, wherein said anchoring means comprises a "C" cross-section formed in the collapsible and self-expanding support ring with the "C" cross-section being open towards the waist section and configured to be coupled to the waist section once the support ring is radially expanded against the outer balloon expandable support.

8. The valve assembly of claim 1, wherein said anchoring means comprises a "V" cross-section formed in the collapsible and self-expanding support ring with the "V" cross-section being open towards the waist section and configured to be coupled to the waist section once the support ring is radially expanded against the outer balloon expandable support.

9. The valve assembly of claim 1, wherein said anchoring means comprises a plurality of tongues radially outwardly extending from the collapsible and self-expanding support ring with the tongues being open towards the waist section and configured to be coupled to the waist section once the support ring is radially expanded against the outer balloon expandable support.

10. The valve assembly of claim 1, wherein said posts and support ring are an integral collapsible piece with each post having a flexible distal free end.

11. The valve assembly of claim 10, wherein said posts and support ring are made of a shape memory material.

12. The valve assembly of claim 11, wherein said material of the posts and support ring is nitinol.

13. The valve assembly of claim 1, wherein said posts and support ring are made of a material comprising stainless steel.

14. The valve assembly of claim 10, wherein each one of the plurality of leaflets has a valley portion thereof fixed to a corresponding portion of the support ring and at least one crest portion thereof fixed at least to the flexible distal free end of a corresponding post.

15. The valve assembly of claim 1, wherein the plurality of leaflets comprises three leaflets.

16. The valve assembly of claim 14, wherein the leaflets are made of natural tissue.

17. The valve assembly of claim 14, wherein the leaflets are made of synthetic material.

18. The valve assembly of claim 14, wherein the support ring is covered by a liner and the leaflets are fixed to the liner.

19. The valve assembly of claim 18, wherein the liner defines said anchoring means.

20. The valve assembly of claim 1, wherein the outer balloon expandable support and the core valve support include respective radiopaque fade-epaque-marks for correct positioning purposes.

21. The valve assembly of claim 1, wherein the outer balloon expandable support is provided, at the inextensible waist section thereof, with a sealing material to seal against the annulus wall of the patient.

\* \* \* \* \*